United States Patent [19]

Aimone

[11] Patent Number: 5,433,737
[45] Date of Patent: Jul. 18, 1995

[54] METHOD FOR THE ELECTRICAL STIMULATION OF A GROUP OF MUSCLES IN ORDER TO IMPROVE THEIR APPEARANCE, AND APPARATUS FOR CARRYING OUT THE METHOD

[75] Inventor: Massimo Aimone, Turin, Italy
[73] Assignee: Medisan S.r.l., Turin, Italy
[21] Appl. No.: 934,527
[22] PCT Filed: Jun. 5, 1990
[86] PCT No.: PCT/EP90/00882
  § 371 Date: Sep. 30, 1992
  § 102(e) Date: Sep. 30, 1992
[87] PCT Pub. No.: WO91/15262
  PCT Pub. Date: Oct. 17, 1991

[30] Foreign Application Priority Data

Mar. 30, 1990 [IT] Italy .................. 67240A90

[51] Int. Cl.⁶ .............................................. A61N 1/36
[52] U.S. Cl. .............................................. 607/72
[58] Field of Search ............... 128/420 R, 421, 423 R, 128/423 W; 607/39-49, 72-76

[56] References Cited

U.S. PATENT DOCUMENTS

| 753,509 | 3/1904 | Munns ................ 128/420 R |
|---|---|---|
| 4,256,116 | 3/1981 | Meretsky et al. .......... 128/421 |
| 4,290,429 | 9/1981 | Blaser . |
| 4,398,537 | 8/1983 | Holmbo ................ 128/420 R |
| 4,813,418 | 3/1989 | Harris .................. 128/421 |
| 4,830,009 | 5/1989 | Schmitt . |
| 4,832,033 | 5/1989 | Maher et al. .............. 607/48 |
| 4,922,906 | 5/1990 | Takeuchi . |
| 4,976,264 | 12/1990 | Petrofsky ............ 128/423 W |
| 5,048,523 | 9/1991 | Yamasawa et al. ........... 128/421 |
| 5,117,826 | 6/1992 | Bartelt et al. ............. 128/421 |
| 5,165,404 | 11/1992 | Andersson et al. .......... 128/421 |

FOREIGN PATENT DOCUMENTS

| 0315768 | 4/1989 | European Pat. Off. . |
|---|---|---|
| 0359982 | 11/1990 | European Pat. Off. . |
| 2129243 | 7/1984 | United Kingdom . |

*Primary Examiner*—William E. Kamm
*Assistant Examiner*—Marianne Parker
*Attorney, Agent, or Firm*—Sughrue, Mion, Zinn, Macpeak & Seas

[57] ABSTRACT

A group of muscles, particularly the glutei, is stimulated electrically by the application of at least one pair of electrodes (18, 19; 20, 21) to the group and the supply of a symmetrically alternating voltage through the electrodes for equal periods of time (A) separated by intervals (B) of predetermined equal duration. In each period of time (A), the alternating voltage has a periodic behaviour with pulses of equal duration (PD) and alternating polarity symmetrical in adjacent half periods and separated by intervals (I) of equal duration. Each period (A) in which the alternating voltage is applied has a duration of between 0.5 and 1.5 s, and the intervals between the periods (A) are between 0.8 and 2 s long. The frequency of the alternating voltage is between 100 and 200 Hz, preferably 150 Hz. Each half period (T/2) in which the voltage is applied includes a pulse having a duration (PD) of between 40 and 60% of the half period.

20 Claims, 4 Drawing Sheets

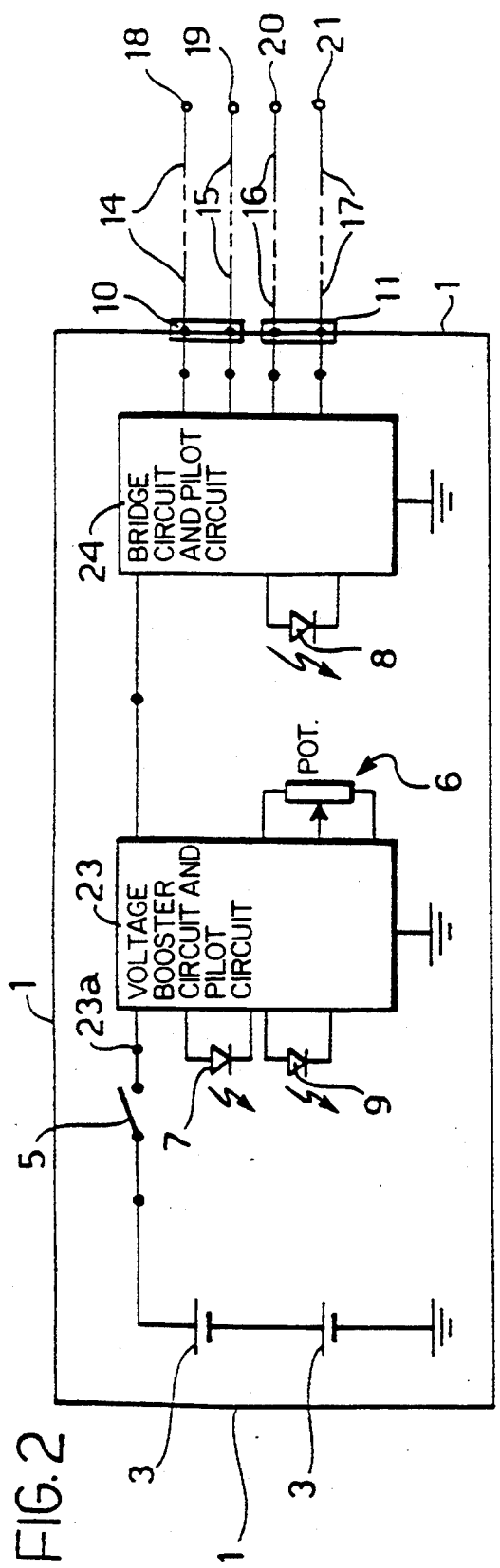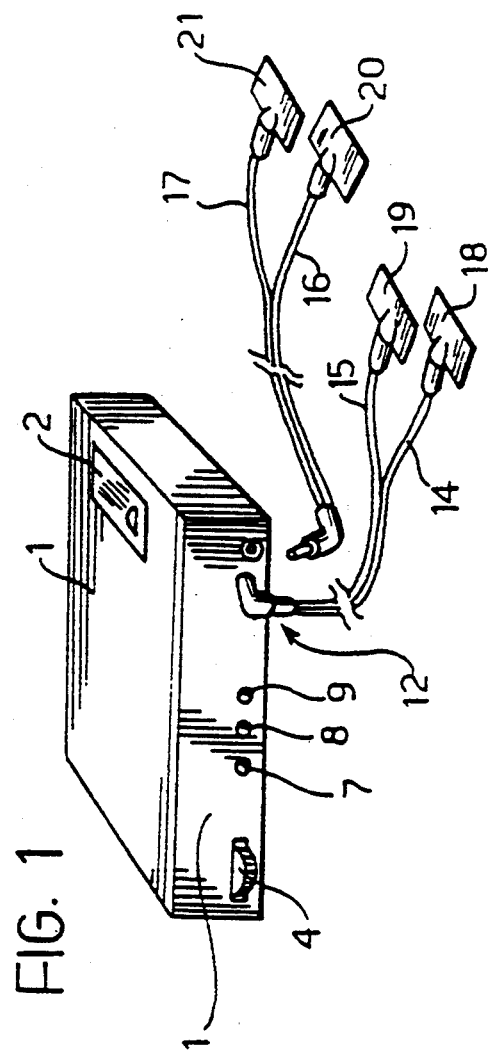

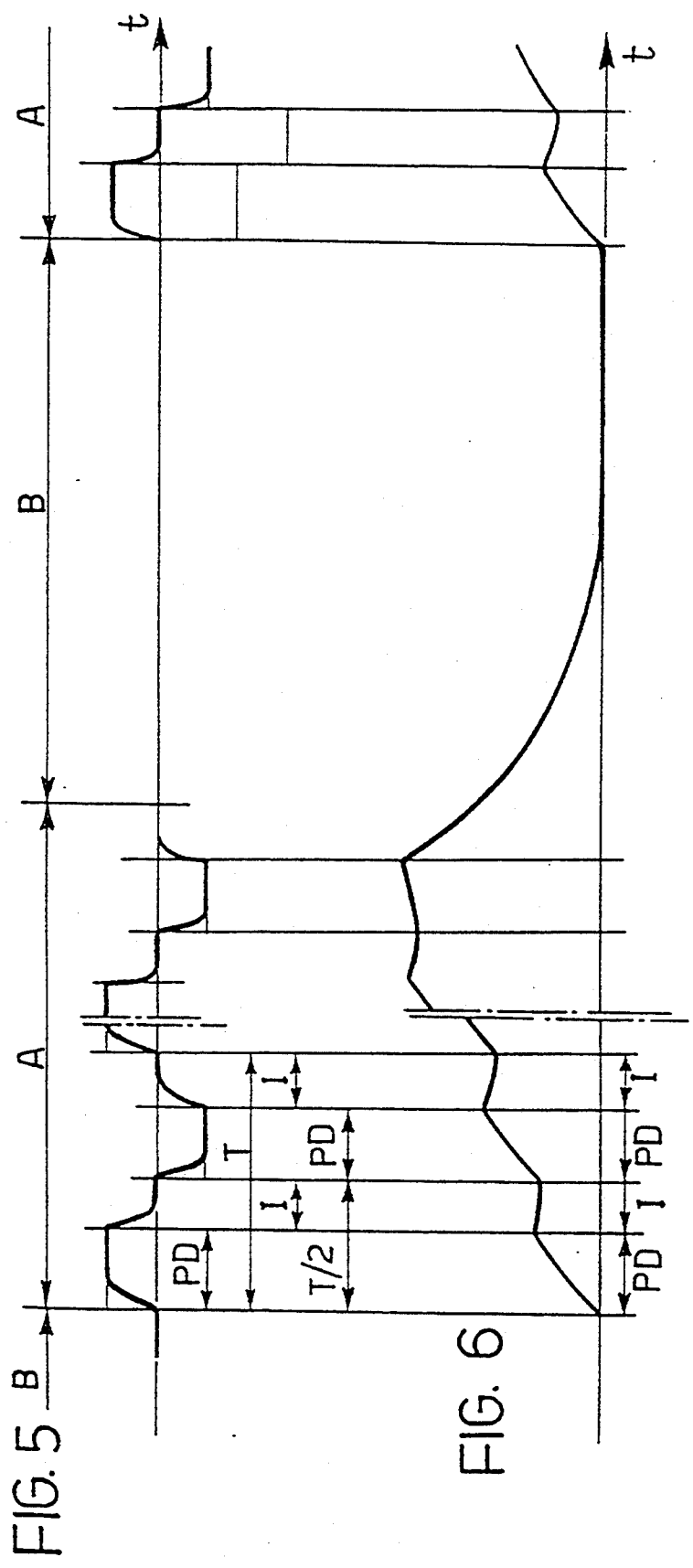
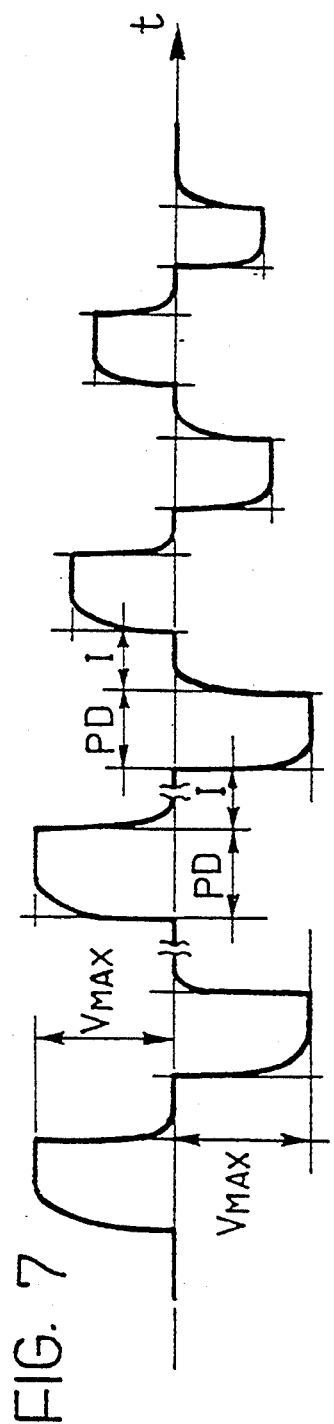
FIG. 5
FIG. 6
FIG. 7

METHOD FOR THE ELECTRICAL STIMULATION OF A GROUP OF MUSCLES IN ORDER TO IMPROVE THEIR APPEARANCE, AND APPARATUS FOR CARRYING OUT THE METHOD

BACKGROUND OF THE INVENTION

The present invention relates to a method and to portable apparatus for the electrical stimulation of a group of muscles, particularly the glutei, in order to improve their appearance and athletic performance.

The use of electrical stimulation has recently become increasingly widespread in the medical and paramedical fields, for example for diagnostic or therapeutic purposes (neuro-electrical investigations, treatment of pain, etc.) or for re-educative purposes (for example in orthopaedics for treating muscles which are relaxed to a greater or lesser extent).

Various methods and apparatus have been proposed for the electrical stimulation of muscle fibres, bundles or groups which are based on the application of unipolar electrical current (that is, one-way or "direct" current) or bipolar current (that is, two-way or "alternating" current) with greatly differing characteristics as regards wave form, amplitude and frequency.

What is more, the present invention falls within the field of application of muscular electrical stimulation, particularly for stimulating the glutei for aesthetic purposes.

It is known that, with advancing age and as a result of ever more widespread sedentary habits, the muscles which are least used habitually, amongst which are the glutei in particular, tend to become slack and lose tone. In the particular case of the glutei, these tend to become flabby and to drop thus adversely affecting the appearance of the anatomical parts concerned.

Active or passive gymnastic exercises or massage have been proposed for preventing this problem but with unsatisfactory results because of the practical difficulties of performing exercises which involve these muscular regions effectively and because of the fatigue which these exercises cause in any case.

The electrical stimulation of these muscles has also been proposed but with the use of non-specific stimulating apparatus, that is, apparatus not expressly designed for stimulating the aforesaid muscles.

In theory, correct electrical stimulation which induces controlled periodic contraction of the muscle group can actually lead to improved muscle tone as well as an increase in contraction capability, in resistance to strain, and in muscle volume.

As already mentioned, the use of conventional, non-specific electrical-stimulation apparatus for stimulating the glutei has, in effect, been unsatisfactory.

It should, in fact, be remembered that, although the different muscles of the body have considerable similarities from a general electrical point of view, each has its own specific qualities and its own particular electrical characteristics (resistance, reactance, etc.) which, in fact, make it a different "electrical load" from the others.

SUMMARY OF THE INVENTION

One object of the present invention, which represents the result of the inventor's ideas and experimental activities, thus lies in the provision of a specific method of process of electrical stimulation, developed particularly for the treatment of the glutei.

A further object of the present invention is constituted by the provision of portable apparatus which is adapted to carry out the electrical-stimulation method or process without the need for connection to the electrical mains supply, and which is therefore more convenient and practical in use and also intrinsically safer from the point of view of accident prevention.

BRIEF DESCRIPTION OF THE DRAWINGS

Further characteristics and advantages of the invention will become clear from the detailed description which follows, with reference to the appended drawings, provided purely by way of non-limiting example, in which:

FIG. 1 is a perspective view of an embodiment of electrical-stimulation apparatus according to the invention, FIG. 2 is an electrical diagram, partially in block form, of the apparatus of FIG. 1, FIG. 5 is a time graph showing an example of the wave form of the voltage applied in use between the output electrodes of the apparatus according to the invention as a function of the time t on the abscissa, FIG. 6 is a graph showing the corresponding contraction and relaxation of the muscle caused by the application of a voltage having the wave form of FIG. 5 as a function of the time t on the abscissa, and FIG. 7 is a further graph showing the wave form of the voltage supplied by the apparatus according to the invention, in a particular operating condition, as a function of the time t on the abscissa.

DETAILED DESCRIPTION OF THE INVENTION

Figure 3:
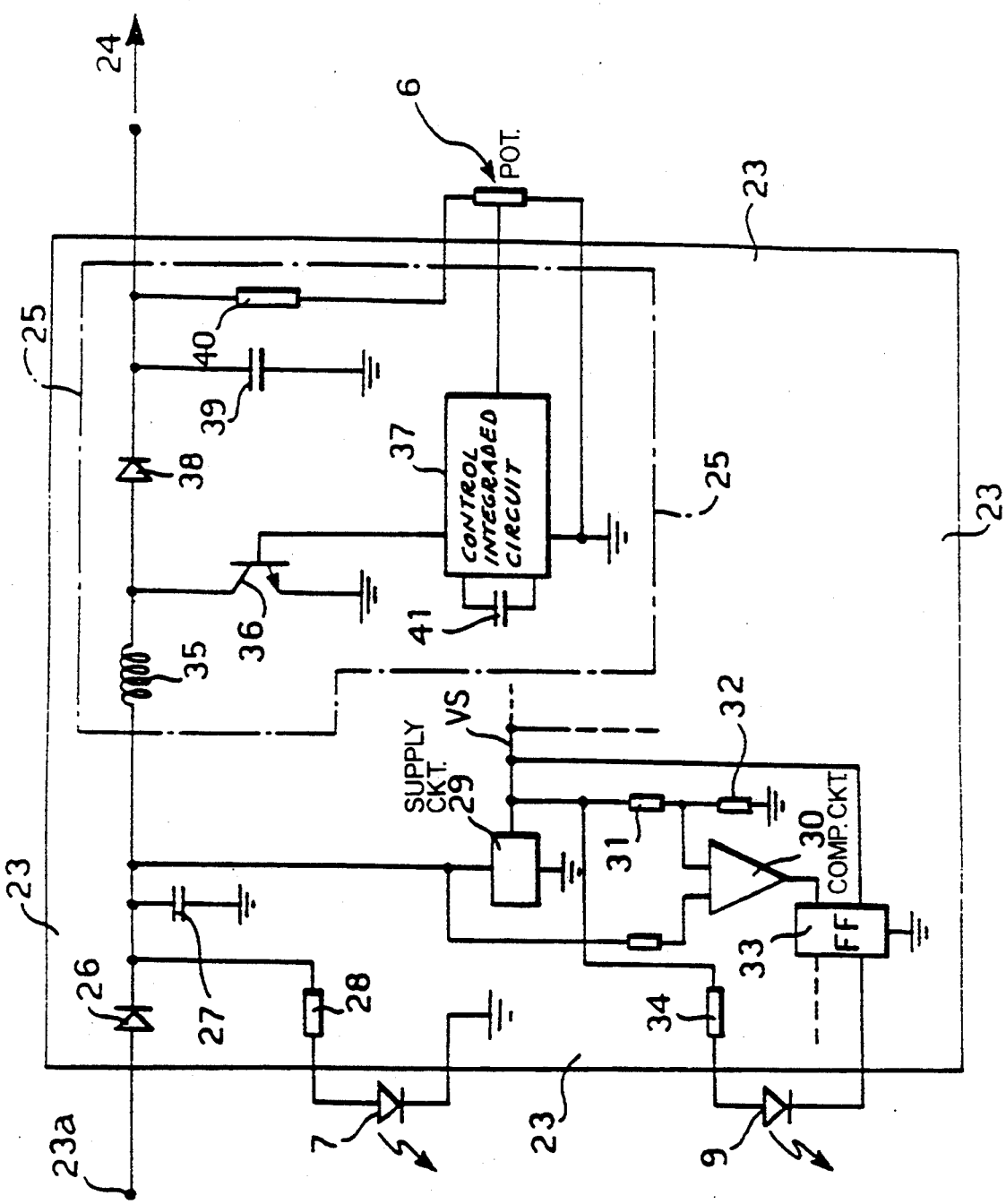
FIG. 3 is a detailed circuit diagram of a first part of the apparatus of FIG. 2.

With reference to FIG. 1, in the embodiment shown, electrical-stimulation apparatus according to the invention comprises a substantially parallelipipedal portable casing 1, for example of moulded plastics material. A compartment, closed by a removable door 2, is defined in the casing and houses a direct-current voltage supply constituted by one or more replaceable or rechargeable storage batteries 3. Typically, the supply may, for example, be a single 9 V battery or by six 1.5 V pen-light batteries.

A knurled wheel, indicated 4 in FIG. 1, is mounted in a slot in the casing 1 and constitutes the manual control member for a supply switch 5 (FIG. 2) and a potentiometer 6 for adjusting the amplitude of the voltage supplied in use.

Three light-emitting diodes, indicated 7, 8 and 9 in FIGS. 1 to 4, are mounted on the casing 1 for providing the user with signals relating to the operating conditions of the apparatus, as will be explained further below.

As can be seen in FIG. 1, the casing 1 also carries two sockets 10 and 11 for accepting bipolar connecting plugs of the so-called "jack" type, indicated 12 and 13. These plugs are connected by pairs of conductors 14, 15 and 16, 17 to respective pairs of electrodes 18, 19 and 20, 21 of known type, for example of conductive elastomeric material.

Each pair of electrodes is intended to be placed in contact with the upper part of a buttock, at the upper and lower ends of the gluteus.

With reference to FIG. 2, two main circuits, indicated 23 and 24, are housed in the casing 1 of the apparatus.

The circuit 23, which will be described in greater detail below with reference to FIG. 3, has an input 23a connected to the supply switch 5 and an output connected to the input of the circuit 24. The latter has outputs connected in order to the output sockets 10 and 11 of the apparatus. The circuit 23 comprises basically a voltage-booster circuit, generally indicated 25 in FIG. 3 and circuits for piloting the light-emitting diodes 7 and 9.

In detail, now, the circuit 23 includes a diode 26 interposed between the input 23a and the input of the cicuit 25 for protection against the reversal of the polarity of the battery or batteries 3. A filtering capacitor 27 is connected between the cathode of the diode 26 and earth.

The light-emitting diode 7 is also connected between the cathode of the diode 26 and earth, in series with a current-limiting resistor 28. In use, the diode 7 is lit each time the supply switch is closed.

A stabilised supply circuit, indicated 29, is connected to the cathode of the diode 26 for supplying a stabilised output voltage $V_s$ of, for example, +5 V to various devices included in the circuits 23 and 24.

When the apparatus is in use, the condition of charge of the batteries 3 is monitored by a comparator circuit, indicated 30 in FIG. 3, which has a first input connected to the cathode of the diode 26 and a second input connected to a supply of a stabilised reference voltage. This supply is formed by means of a voltage divider connected to the output of the circuit 29 and including two resistors 31 and 32. The comparator circuit 30 is connected to an input of a bistable circuit (flip-flop) indicated 33. The light-emitting diode 9 has its cathode connected to the output of the supply circuit 29 through a resistor 34 and its anode connected to an output of the bistable circuit 33.

When the comparator circuit 30 detects that the voltage supplied by the batteries 3 has fallen below a threshold (preset by means of the divider 31-32), it switches the state of the bistable circuit 33 and the output of the latter, which is connected to the diode 9, is switched to the "low" level causing the light-emitting diode to be lit. The user is thus warned of the need to replace or recharge the batteries.

Conveniently, the other input of the bistable circuit 33 is connected to the output of the supply circuit 29. Moreover, the other output of the bistable circuit 33 can be used, to advantage, for preventing the operation of the circuits 25 and 24, in fact de-activating the apparatus when the level of charge of the batteries 3 falls below the preset threshold. In this case, the apparatus can be re-enabled only by the "resetting" of the bistable circuit 33 as a result of the replacement or recharging of the batteries.

The voltage-booster circuit 25 comprises essentially a "step-up" circuit and includes a storage inductor 35 with one terminal connected to the cathode of the diode 26 and the other terminal connected to the collector of a transistor 36. The latter has its emitter connected to earth and its base connected to the output of a control circuit 37 which may be constituted, for example, by a TL497 integrated circuit produced by Texas Instruments.

The anode of a diode 38 is connected to the coil 35 and its cathode is connected to a first plate of a capacitor 39 whose other plate is connected to earth. The non-earthed plate of the capacitor 39 represents the output of the circuit 23 as a whole and is connected to the input of the circuit 24. A voltage divider including a resistor 40 and the potentiometer 6 mentioned above is connected between this plate of the capacitor 39 and earth. The slider of the potentiometer is connected to an input of the control circuit 37.

A capacitor 41 is connected between two terminals of the control circuit 37. If this circuit is constituted by the integrated circuit TL497, the capacitor 41 is connected between the pins 4 and 14 of that device.

The function of the capacitor 41 is essentially that of limiting the maximum time for which the transistor 36 is conductive to a preset value. As can be seen more clearly from the following, the effect of this capacitor is in fact to limit the time for which the circuit 25 supplies the maximum possible supply voltage to the circuit 24.

In operation, the integrated circuit 37 switches the transistor between the non-conductive and conductive conditions at a high frequency. When the transistor is conductive, the capacitor 39 is disconnected from the inductor and energy is stored in the latter. Each time the transistor 36 is made non-conductive, the inductor 35 is connected to the capacitor 39 through the diode 38 and that capacitor is charged by the current which reaches it through the diode. The voltage between the plates of the capacitor increases correspondingly by a certain amount. The voltage across the capacitor 39 can thus be brought, by successive stepped increments, to a value considerably higher than the overall voltage supplied by the batteries 3.

In known manner, the control circuit 37 pilots the transistor 36 in a predetermined manner in dependence on the voltage reached across the capacitor 39 which is detected by means of the divider formed by the resistor 40 and the potentiometer 6. The circuit 37 brings the voltage across the capacitor 39 to different values, which can be varied, for example, between 50 and 100 volts, according to the position of the movable slider of the potentiometer (which can be altered by the user by means of the wheel 4).

Figure 4:
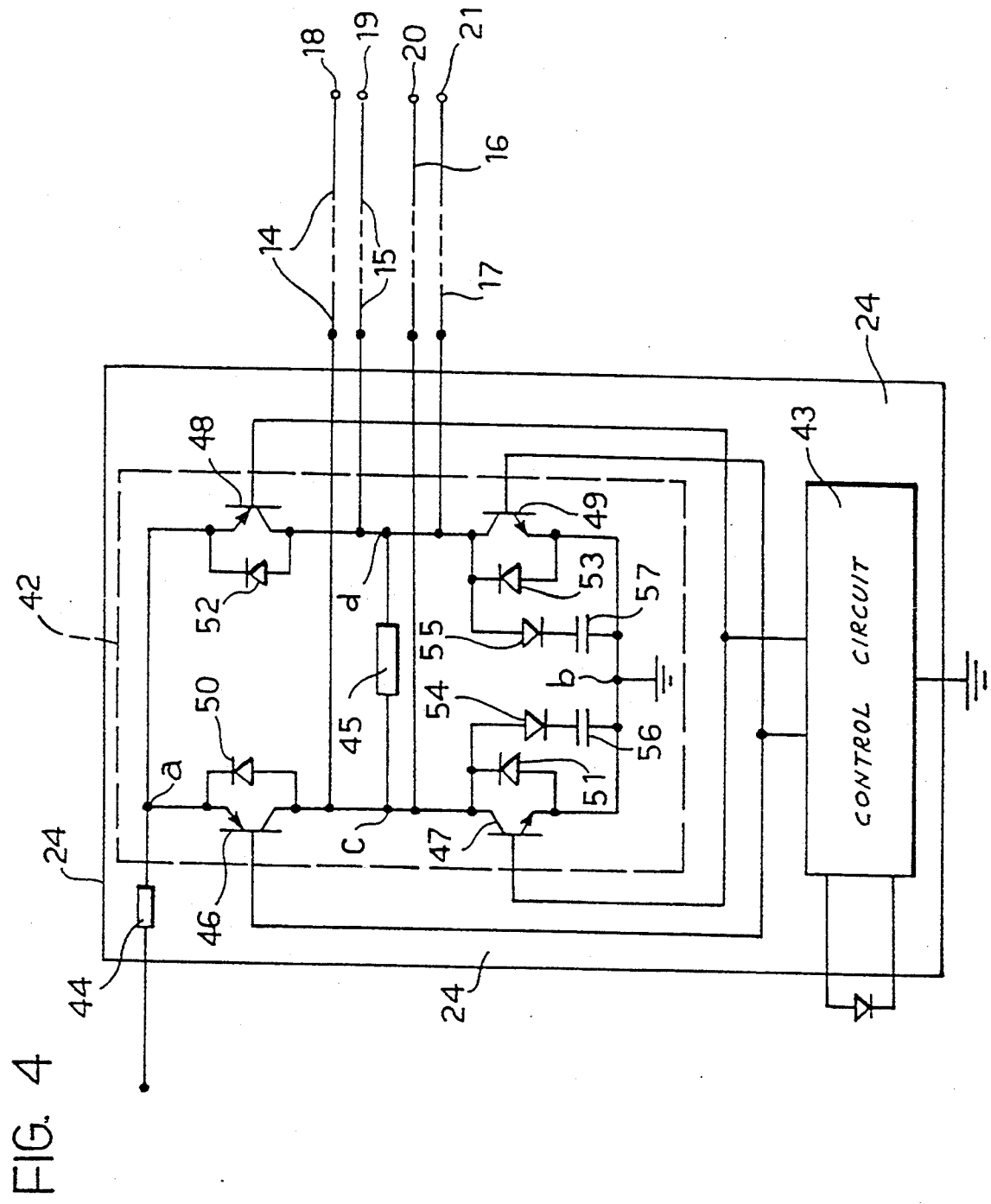
FIG. 4 is a detailed electrical diagram of a second part of the apparatus.

With reference to FIG. 4, the circuit 24 comprises essentially an H-type bridge circuit 42 and an associated piloting circuit 43.

The bridge circuit has two opposite pairs of junctions or nodes, a, b and c, d. The junctions or nodes a and b are connected to the output of the circuit 23, through a resistor 44, and to earth respectively. The junctions c and d are connected, in use, to homologous electrodes 18, 20 and 19, 21 of the two pairs of electrodes respectively. An output resistor 45 is connected between the junctions c and d.

As is seen from FIG. 4, respective electronic switches, constituted by transistors 46 to 49, are provided in the four sides of the bridge circuit 42 defined between adjacent pairs of junctions or nodes. The transistors 46 and 48 of the upper sides of the bridge are of the pnp type while the transistors 47 and 49 are of the npn type.

Respective diodes 50 to 53 are connected in parallel with the collector-emitter paths of the transistors.

The bases of the transistors 46 to 49 are connected to corresponding outputs of the piloting circuit 43. In particular, the bases of the transistors 46 and 49 and the bases of the transistors 47 and 48 are piloted by two different outputs of the circuit 43.

The piloting circuit 43 is arranged, in known manner, to pilot the two pairs of opposite transistors 46, 49 and 47, 48 of the bridge in an alternating on/off manner at a predetermined frequency (for example 300 Hz) so as to cause current to flow alternately in the resistor 45 in one direction and the other. Consequently, in operation, a voltage whose sign or polarity reverses cyclically appears between the electrodes 18 and 19 and, correspondingly, between the electrodes 20 and 21, in the manner which will be described further below.

Two filtering circuits including respective diodes 54 and 55 in series with associated capacitors 56 and 57 are provided in parallel with the collector-emitter paths of the lower transistors 47 and 49 of the bridge. As will become clearer from the following, these filtering circuits are intended to attenuate the fronts of the alternating voltage which is applied between the electrodes 18, 19 and 20, 21 in use.

The light-emitting diode 8 is connected to the piloting circuit 43 associated with the bridge circuit 42. In use, the piloting circuit controls the light-emitting diode 8 so as to provide an intermittent optical signal whose frequency is linked to the frequency of the alternating voltage applied between the electrodes in operation.

In use, the electrodes 18, 19 and 20, 21 are applied to the glutei. In particular, one electrode of each pair is applied to the top part of the gluteus, whilst the other electrode is applied to the lower part.

In order to reduce the contact resistance, a conductive gel may conveniently be interposed between each electrode and the skin.

The user then closes the supply switch 5 by means of the wheel 4. With the aid of the same wheel, the user varies the position of the movable slider of the potentiometer 6 and, in practice, sets the desired stimulation intensity.

In fact, the voltage of the direct current supplied by the circuit 23 to the circuit 24 varies according to the position of the potentiometer slider.

The piloting circuit 43, which includes a clock generator and associated logic circuits, is arranged to pilot the transistors 46 to 49 of the bridge circuit so that, in use, a symmetrical alternating voltage is developed across the output resistor 45 with time periods of equal duration, separated by intervals whose predetermined durations are equal to each other. FIG. 5 shows, by way of example, the wave form of the voltage established across the output resistor 45 and hence between each pair of electrodes of the apparatus in operation. In this drawing, the time periods during which the symmetrical alternating voltage is applied are indicated A and the intervals separating them are indicated B.

On the basis of tests carried out by the inventor, it has been found that the best stimulation results are obtained by the application of the symmetrical alternating voltage between the electrodes for time periods of between 0.5 and 1.5 seconds, preferably 0.8 seconds, duration separated by intervals of between 0.8 and 2 seconds, preferably 1 second, duration.

During each time period A, the the symmetrical alternating voltage to advantage has a frequency $f=1/T$ between 100 and 200 Hz, preferably 150 Hz.

As is seen from FIG. 5, the symmetrical alternating voltage applied during each time period A has a periodic behaviour with a period T and a symmetrical wave form in the two half-periods T/2. In two consecutive half periods, the wave form exhibits pulses of equal duration and opposite polarity separated by intervals of equal duration.

Conveniently, in each half period, the voltage pulse has a duration PD of between 40 and 60% of the half period. Correspondingly, the intervals I (FIG. 5) between two consecutive pulses have durations of between 60% and 40% of the half period.

Tests carried out have indicated, however, that the best results in terms of the tolerableness and acceptability of the electrical stimulation are achieved with pulses whose duration is nearer to 60% of the half period, rather than with pulses whose duration is nearer to 40%.

FIG. 6 is a graph showing, by way of example and as a function of time, the magnitude of the contraction of the gluteus corresponding to the application of the voltage shown graphically in FIG. 5.

As is seen from FIG. 6, for each time period A in which the alternating voltage is applied, there is a corresponding phase in which the muscle contracts incrementally. More particularly, each voltage pulse, whatever its polarity, causes an increase in the contraction of the gluteus. In the interval between two pulses, the gluteus relaxes partially. The maximum contraction is therefore reached gradually towards the end of each time period A, passing through a sequence of periods of contraction intercalated with intervals of relaxation. The most contracted condition of the muscle is therefore reached progressively through alternating contractions and relaxations, and thus with an effect comparable to that of a massage.

During each interval B between two time periods A in which the symmetrical alternating voltage is applied, the muscle relaxes completely with its own relaxation time constant.

As can be seen in FIG. 5, the rising and falling fronts of the symmetrical alternating voltage pulses applied in each time period A are somewhat blunted, that is rounded, as a result of the filtering effect of the capacitors 56 and 57 of the bridge circuit 42 in combination with the resistor 44. In fact, the combined effect of this resistor and each of the capacitors introduces a time constant which makes the rise and fall of the voltage in each pulse more gradual. In effect, this essentially has a "low-pass" filtering action which effectively limits the presence of high-frequency components in the voltage applied between the electrodes. Thus, the associated diathermal effects, that is, localised heating of the skin and reddening, which typically occur during electrical stimulation with conventional apparatus are reduced drastically.

As stated above, the intensity of the stimulation is adjustable by the user with the aid of the control wheel 4 which acts on the potentiometer 6. For reasons of safety, however, in the apparatus according to the invention, the maximum time for which the voltage is delivered at the maximum amplitude which can be set is limited automatically. This is to prevent problems should the apparatus be used incorrectly.

The maximum time for which the maximum voltage is supplied is limited, as stated above, by the selection of the capacitance of the capacitor 41 connected to the control circuit 37 which controls the transistor 36 of the voltage-booster circuit 25.

When the user positions the wheel 4 in the position corresponding to the application of a voltage of maximum amplitude $V_{max}$, a symmetrical alternating voltage which for a certain period, for example 0.2–0.3 seconds, assumes the amplitude $V_{max}$, is in fact supplied between each pair of electrodes. When this period of time has elapsed, the voltage supplied decreases gradually and automatically as shown in FIG. 7.

This happens because the capacitor 41 limits the maximum "on" time of the transistor 36 and, when this has elapsed, the capacitor 39 starts to discharge gradually and the voltage of the direct current output by the circuit 23 reduces correspondingly.

Tests carried out have shown that the application of a voltage having the characteristics described above between each pair of electrodes achieves effective stimulation of the gluteus which, at the same time, is acceptable and even pleasant.

what is claimed is:

1. Portable apparatus for electrical stimulation of a group of muscles comprising:
   at least one storage battery,
   at least one pair of electrodes for application to the group of muscles, and
   circuit means connected to the at least one battery and to the at least one pair of electrodes to output a voltage of predetermined characteristics to the at least one pair of electrodes;
   wherein the circuit means comprise voltage-booster circuit means connected to the at least one battery for boosting the voltage,
   bridge circuit means comprising a plurality of electronic switches having control inputs, said electronic switches being connected to the voltage-booster circuit means and connected to the at least one pair of electrodes for providing the voltage to the at least one pair of electrodes; and
   piloting circuit means connected to the control inputs of the electronic switches to pilot the electronic switches so that, in operation, a symmetrical alternating voltage is applied cyclically between the at least one pair of electrodes for time periods of equal duration separated by intervals of predetermined equal duration; the alternating voltage in each of the time periods having periodic behaviour which is symmetrical in consecutive half periods, with pulses of equal duration and alternating polarity separated by intervals of equal duration.

2. Apparatus according to claim 1, wherein said piloting circuit means provides the time periods in which the alternating voltage is applied with a duration of between 0.5 and 1.5 seconds and the intervals between the time periods with a duration of between 0.8 and 2 seconds.

3. Apparatus according to claim 1, wherein said piloting circuit means provides the alternating voltage in each of the time periods with a frequency of between 100 and 200 Hz.

4. Apparatus according to claim 3, wherein said piloting circuit means provides each half period with a pulse whose duration is between 40 and 60% of the half period.

5. Apparatus according to claim 1, further comprising manual adjustment and operating means for enabling an amplitude of the alternating voltage applied between the at least one pair of electrodes in use to be varied within a predetermined range.

6. Apparatus according to claim 5, wherein the adjustment and operating means enables the amplitude of the alternating voltage to be varied between 50 and 100 volts.

7. Apparatus according to claim 5, wherein the voltage-booster circuit means includes means for limiting a time for which a maximum voltage which can be set by the adjustment and operating means is supplied.

8. Apparatus according to claim 1, wherein the bridge circuit means is of an H type and includes four sides in each of which there is one of the electronic switches; the bridge circuit means including first and second pairs of opposite junctions, the first pair of opposite junctions of the bridge circuit means being connected to an output of the voltage-booster circuit means and the second pair of opposite junctions being interconnected by an impedance and connected to the at least one pair of electrodes.

9. Apparatus according to claim 8, wherein the bridge circuit means has associated filtering circuit means of a low-pass type, for attenuating fronts of the alternating voltage which is applied between the at least one pair of electrodes.

10. Apparatus according to claim 9, wherein respective capacitive snubber circuits are provided in parallel with two electronic switches of two adjacent sides of the bridge circuit means.

11. Apparatus according to claim 1, wherein the voltage-booster circuit means comprises:
    an output capacitor,
    a storage inductor connected to the at least one battery,
    an electronic switch connected between the output capacitor and the storage inductor and having a first condition in which the electronic switch disconnects the output capacitor from the storage inductor and enables current to flow from the battery to the storage inductor, and a second condition in which the electronic switch connects the storage inductor to the output capacitor to enable the output capacitor to be charged;
    detector means for detecting a voltage across the output capacitor, and
    a control circuit means connected to the detector means for piloting the electronic switch in an on-/off manner predetermined in dependence on the voltage across the output capacitor.

12. Apparatus according to claim 11, wherein the control circuit means includes means for limiting a maximum time for which the electronic switch can be kept in the first condition.

13. Apparatus according to claim 11, wherein the detector means for detecting the voltage across the output capacitor comprises a resistive divider and adjusting means for adjusting the amplitude of the voltage comprised of a hand-operated potentiometer which forms part of the resistive divider.

14. Apparatus according to claim 1, further comprising sensor means for sensing a level of charge of the at least one battery and for activating first indicator means for indicating a low charge when the at least one battery has a low charge.

15. Apparatus according to claim 1, wherein a hand-operable control switch is interposed between the at least one battery and the voltage-booster circuit means, and a second indicator means is provided indicating when the hand operable control switch is closed.

16. Apparatus according to claim 15, further comprising third indicator means controlled by the piloting circuit means associated with the bridge circuit means for supplying an intermittent signal whose frequency is linked to a frequency of the alternating voltage applied, in use, between the at least one pair of electrodes.

17. A method for electrical stimulation of a group of muscles in order to improve their appearance, comprising the steps of applying at least one pair of electrodes to the group of muscles; and generating and applying an electrical voltage of predetermined characteristics between the at least one pair of electrodes;

wherein said electrical voltage is a symmetrical alternating voltage and is applied cyclically between the at least one pair of electrodes for time periods of equal duration separated by intervals of predetermined equal length; an alternating voltage in each of the time periods having periodic behaviour which is symmetrical in adjacent half periods, with pulses of equal duration and alternating polarity separated by intervals of equal duration and wherein the time periods in which the alternating voltage is applied have durations of between 0.5 and 1.5 seconds and the intervals between the time periods have durations of between 0.8 and 2 seconds.

18. A method according to claim 17, wherein the voltage in each of the time periods alternates at a frequency of between 100 and 200 Hz, preferably 150 Hz.

19. A method according to claim 18, wherein each half period includes a pulse whose duration is between 40 and 60% of the half period.

20. A method according to claim 17, wherein an amplitude of the alternating voltage is variable between 50 and 100 volts.

* * * * *